US007629160B2

(12) United States Patent
Webb et al.

(10) Patent No.: US 7,629,160 B2
(45) Date of Patent: Dec. 8, 2009

(54) VECTORS AND METHODS FOR ENHANCED CELL LONGEVITY AND PROTEIN EXPRESSION

(75) Inventors: Bruce Allen Webb, Lexington, KY (US); Jeremy Kroemer, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 0 days.

(21) Appl. No.: 11/016,871

(22) Filed: Dec. 21, 2004

(65) Prior Publication Data

US 2006/0134743 A1 Jun. 22, 2006

(51) Int. Cl.

| | |
|---|---|
| *C12P 21/06* | (2006.01) |
| *C12N 1/20* | (2006.01) |
| *C12N 15/00* | (2006.01) |
| *C07H 21/02* | (2006.01) |

(52) U.S. Cl. ................ 435/252.3; 435/69.1; 435/320.1; 536/23.1

(58) Field of Classification Search ................ 435/69.1; 514/12

See application file for complete search history.

(56) References Cited

U.S. PATENT DOCUMENTS 5,827,518 A 10/1998 Webb et al.

OTHER PUBLICATIONS

Smith et al., Modification and secretion of human interleukin 2 produced in insect cells by a baculovirus expression vector, Proc. Natl. Acad. Sci. USA, vol. 82, p. 8404-8408 (Dec. 1985).*
GenCore version 5.1.6, Result 2 pp. 1-2, Result 2.*
GenCore vesrion 5.1.6 for SEQ ID No. 1 (pp. 1-2).*
Blissard wt al., Segment W of Campoletis onorensis virus: expression, gene products, and organization, Virology, 169(1), p. 78-89.*
Webb et al., GenBank Accession No. AY029396. Campoletis sonorensis ichnovirus, segment P, complete sequence. (Sep. 9, 2002).*
Volkoff et al., Virology Sep. 1, 2002; 300(2):316-31.
Kroemer. J.A., and Webb, B.A. 2004. Brisbane, Queensland, Australia, submitted Mar. 31, 2004.
Kroemer, J.A., and Webb, B.A. 2004. Montreal, Canada, submitted Jan. 28, 2004.
Cuit and Webb, J.Gen. Virol. (1997) 78:1807=1817.
Soldevilla and Webb, J. Gen. Virol (1998) 77:1379-1388.
Li and Webb, J. Virol. (1994) 68(11);7482-7489.
Dib-Hajj et al., Proc. Natrl. Acad. Soi. (USA) 90: 3765 (1993).
Summers et al., Proc. Natl. Acad. Sci. (USA) 92: 29 (1995).

* cited by examiner

*Primary Examiner*—Christian L Fronda
(74) *Attorney, Agent, or Firm*—McDermott Will & Emery LLP

(57) ABSTRACT

It is the object of the current invention to provide methods and compositions relating to the expression of vankyrin proteins in cell lines to increase their viability, longevity and capacity for protein production. The inventors have discovered that the expression of P-ank-1 and $I^2$-ank-3 proteins in cell culture has increased the cells' longevity and capacity for endogenous and/or heterologous target protein production. Specifically, the present invention relates to the enhanced expression of endogenous and/or heterologous target proteins/polypeptides in recombinant cells that are also expressing P-ank-1 and/or $I^2$-ank-3 protein compared to expression host cells that are not expressing P-ank-1 and/or $I^2$-ank-3 protein.

24 Claims, 6 Drawing Sheets

|        | M | 1D | 2D | 3D | 4D | 5D | 6D | 7D | Specificity |
|--------|---|----|----|----|----|----|----|----|-------------|
| P-ank-1 |   |    |    |    |    |    |    |    | Fat Body |
| P-ank-2 |   |    |    |    |    |    |    |    | Hemocyte/Fat Body |
| P-ank-3 |   |    |    |    |    |    |    |    | Hemocyte |
| P-ank-4 |   |    |    |    |    |    |    |    | Hemocyte |
| I2-ank-1 |  |    |    |    |    |    |    |    | Hemocyte |
| I2-ank-2 |  |    |    |    |    |    |    |    | Fat Body/Hemocyte |
| I2-ank-3 |  |    |    |    |    |    |    |    | Fat Body |

Figure 2

P-ankyrin-1: cDNA (SEQ ID NO: 1)

ATGGAGATTTCTCAAATTCGAAAGCTATTCGGTAAAAACCGCGTCACGAAAAATACCATATTTC
ACGAGCTTGCCCACGCTGGATCATTGACACTACTGTACCGGGTTCGAGACAACATTGACGAGCC
ATGCAGCTCTATCCTGCAAGAGGTTAATGCTGATGGAGACTATAGTATCCATGTGGCGGCAAAG
ACGCACCGAGGACAGCTTGCAGTGAGGATCATACAGGTGCTACTAGAGTTAGGGGCAAACCTGA
ATGCAAAGATCGTGTCTGGAACTTTACTGTACTGCATGTCGCAGTTGAGCGAGACGATTACGT
CCTCGCAAAGTGGCTGCGCCATCACCCACAAATTGATTTGGATGCAAGAGGTTGGGATGGACTT
ACGGCACATGAAACGTCGTTGATAACGTGCAACAAAGAGATGATGGATATTTTCCGAACCGACG
GTGTTAACAGAGCCGGTGGTACAGAGCCGAAAGTGAATGAAAGTACATCGAATGACAATCAGCA
T

P-ankyrin-1: Protein (SEQ ID NO: 2)

MEISQIRKLFGKNRVTKNTIFHELAHAGSLTLLYRVRDNIDEPCSSILQEVNADGDYSIHVAAK
THRGQLAVRIIQVLLELGANLNAKDRVWNFTVLHVAVERDDYVLAKWLRHHPQIDLDARGWDGL
TAHETSLITCNKEMMDIFRTDGVNRAGGTEPKVNESTSNDNQH

I²-ankyrin-3: cDNA (SEQ ID NO: 3)

ATGGAAAATTCTCAAATTGCAAAGCTGTTCGGTACAAACTGGGTCACGAAAAATACCATATTTC
ACGAGCTTGCCCACGCTGGATCGTTGACACTTCTTCACCGGGTTCGACACAACATTCAAGAGCC
ATGCAGCTCTATCCTGCAAGAGGTTAATGCTAATGGAGACTATAGTATTCATGTGGCGGCAAAA
ACGCACCGAGGACAGCTCGCAGTGAGGATCATTCAGATACTACTGGAATTGGGGGCTAATCTGA
ATGCAAGAGATCGTGTCTGGAACTTTACTGTACTGCATGTCGCAGTTGAGCGGGAGGATTACGT
CCTCACAATGTGGCTGCGCCATCACCCACAAATGGATTTGAATGCGAGAGGTTTCGCTGGACTT
ACGGCACATCAAATGGCGTTGATGTCGTGCGACAGAAAGATGATGGATATTTTCCGAACCGACG
CTGTATACGGAGCCGGTGGTTCAGAGCCGAAAGTGAATGAAAGTACATCGAATGACAATCAGCA
T

I²-ankyrin-3: Protein (SEQ ID NO: 4)

MENSQIAKLFGTNWVTKNTIFHELAHAGSLTLLHRVRHNIQEPCSSILQEVNANGDYSIHVAAK
THRGQLAVRIIQILLELGANLNARDRVWNFTVLHVAVEREDYVLTMWLRHHPQMDLNARGFAGL
TAHQMALMSCDRKMMDIFRTDAVYGAGGSEPKVNESTSNDNQH

Figure 3

Approximate Yields of Vankyrin Proteins off of Nickel-NTA Columns (QIAGEN)

| | Average Concentration of Eluted Proteins (from 25mL Culture) | Approximate Yield (1L Culture) |
|---|---|---|
| P-ank-1 | 1.22 mg/mL (in 2.05mL) | 100.04 mg/L |
| P-ank-2 | 0.9035 mg/mL (in 1.50mL) | 54.21 mg/L |
| P-ank-3 | 1.009 mg/mL (in 1.360mL) | 54.89 mg/L |
| P-ank-4 | 0.9904 mg/mL (in 1.500mL) | 59.42 mg/L |
| I2-ank-1 | 0.9382 mg/mL (in 1.500mL) | 56.29 mg/L |
| I2-ank-2 | 1.002 mg/mL (in 1.500mL) | 60.12 mg/L |
| I2-ank-3 | 1.18 mg/mL (in 2.050mL) | 96.76 mg/L |

Approximate purity of eluted proteins: 60-75%

Proteins were collected 1 day prior to apparent cell lysis in infected Sf9 Cells Yield Calculation: 1.22mg/mL X 2.05 mL = 2.501 mg
2.501mg/.025L Culture = 100.04 mg/L

Figure 6

```
                          SEQUENCE LISTING

<160> NUMBER OF SEQ ID NOS: 4

<210> SEQ ID NO 1
<211> LENGTH: 513
<212> TYPE: DNA
<213> ORGANISM: Campoletis sonorensis

<400> SEQUENCE: 1
atggagattt ctcaaattcg aaagctattc ggtaaaaacc gcgtcacgaa aaataccata      60
tttcacgagc ttgcccacgc tggatcattg acactactgt accgggttcg agacaacatt     120
gacgagccat gcagctctat cctgcaagag gttaatgctg atggagacta tagtatccat     180
gtggcggcaa agacgcaccg aggacagctt gcagtgagga tcatacaggt gctactagag     240 ttagggcaa acctgaatgc gaaagatcgt gtctggaact ttactgtact gcatgtcgca     300
gttgagcgag acgattacgt cctcgcaaag tggctgcgcc atcacccaca aattgatttg     360
gatgcaagag gttgggatgg acttacggca catgaaacgt cgttgataac gtgcaacaaa     420
gagatgatgg atattttccg aaccgacggt gttaacagag ccggtggtac agagccgaaa     480
gtgaatgaaa gtacatcgaa tgacaatcag cat                                  513

<210> SEQ ID NO 2
<211> LENGTH: 171
<212> TYPE: PRT
<213> ORGANISM: Campoletis sonorensis

<400> SEQUENCE: 2

Met Glu Ile Ser Gln Ile Arg Lys Leu Phe Gly Lys Asn Arg Val Thr
1

```
Gln Glu Val Asn Ala Asp Gly Asp Tyr Ser Ile His Val Ala Ala Lys
     50                  55                  60

Thr His Arg Gly Gln Leu Ala Val Arg Ile Ile Gln Val Leu Leu Glu
 65                  70                  75                  80

Leu Gly Ala Asn Leu Asn Ala Lys Asp Arg Val Trp Asn Phe Thr Val
                 85                  90                  95

Leu His Val Ala Val Glu Arg Asp Tyr Val Leu Ala Lys Trp Leu
                100                 105                 110

Arg His His Pro Gln Ile Asp Leu Asp Ala Arg Gly Trp Asp Gly Leu
                115                 120                 125

Thr Ala His Glu Thr Ser Leu Ile Thr Cys Asn Lys Glu Met Met Asp
                130                 135                 140

Ile Phe Arg Thr Asp Gly Val Asn Arg Ala Gly Gly Thr Glu Pro Lys
145                 150                 155                 160

Val Asn Glu Ser Thr Ser Asn Asp Asn Gln His
                165                 170

<210> SEQ ID NO 3
<211> LENGTH: 513
<212> TYPE: DNA
<213> ORGANISM: Campoletis sonorensis

<400> SEQUENCE: 3
atggaaaatt ctcaaattgc aaagctgttc ggtacaaact gggtcacgaa aataccata      60 tttcacgagc ttgcccacgc tggatcgttg acacttcttc accgggttcg acacaacatt    120
caagagccat gcagctctat cctgcaagag gttaatgcta atggagacta tagtattcat    180
gtggcggcaa aaacgcaccg aggacagctc gcagtgagga tcattcagat actactggaa    240
ttgggggcta atctgaatgc aagagatcgt gtctggaact ttactgtact gcatgtcgca    300
gttgagcggg aggattacgt cctcacaatg tggctgcgcc atcacccaca aatggatttg    360
aatgcgagag gtttcgctgg acttacggca catcaaatgg cgttgatgtc gtgcgacaga    420
aagatgatgg atattttccg aaccgacgct gtatacggag ccggtggttc agagccgaaa    480
gtgaatgaaa gtacatcgaa tgacaatcag cat                                 513

<210> SEQ ID NO 4
<211> LENGTH: 171
<212> TYPE: PRT
<213> ORGANISM: Campoletis sonorensis

<400> SEQUENCE: 4

Met Glu Asn Ser Gln Ile Ala Lys Leu Phe Gly Thr Asn Trp Val Thr
 1               5                  10                  15

Lys Asn Thr Ile Phe His Glu Leu Ala His Ala Gly Ser Leu Thr Leu
                 20                  25                  30

Leu His Arg Val Arg His Asn Ile Gln Glu Pro Cys Ser Ser Ile Leu
                 35                  40                  45

Gln Glu Val Asn Ala Asn Gly Asp Tyr Ser Ile His Val Ala Ala Lys
     50                  55                  60

Thr His Arg Gly Gln Leu Ala Val Arg Ile Ile Gln Ile Leu Leu Glu
 65                  70                  75                  80

Leu Gly Ala Asn Leu Asn Ala Arg Asp Arg Val Trp Asn Phe Thr Val
                 85                  90                  95

Leu His Val Ala Val Glu Arg Glu Asp Tyr Val Leu Thr Met Trp Leu
                100                 105                 110
```

-continued

```
Arg His His Pro Gln Met Asp Leu Asn Ala Arg Gly Phe Ala Gly Leu
        115                 120                 125

Thr Ala His Gln Met Ala Leu Met Ser Cys Asp Arg Lys Met Met Asp
        130                 135                 140

Ile Phe Arg Thr Asp Ala Val Tyr Gly Ala Gly Gly Ser Glu Pro Lys
145                 150                 155                 160

Val Asn Glu Ser Thr Ser Asn Asp Asn Gln His
                165                 170
```

VECTORS AND METHODS FOR ENHANCED CELL LONGEVITY AND PROTEIN EXPRESSION

BACKGROUND OF THE INVENTION

1. Field of the Invention

This invention relates to the fields of nucleic acid constructs and cell lines that allow for the increased expression of endogenous or heterologous target protein.

2. Background

The immediate challenge created by the genomics era is the production of the novel proteins to understand their function. Current methods of expressing genes in a mammalian cell include the use of viral vectors, such as those which are derived from retroviruses, adenoviruses, herpes viruses, vaccinia viruses, polio viruses, sindbis viruses, or adeno-associated viruses. Other methods of expressing an exogenous gene in a mammalian cell include direct injection of DNA, the use of ligand-DNA conjugates, the use of adenovirus-ligand-DNA conjugates, calcium phosphate precipitation, and methods which utilize a liposome- or polycation-DNA complex.

Due to its advantages in versatility and speed, the Baculovirus Expression Vector System (BEVS) used in conjunction with insect cells has become well-established for the production of proteins, particularly recombinant glycoproteins. Baculovirus mediated protein expression provides correct folding of recombinant protein as well as disulfide bond formation, oligomerization and other important post-translational modifications that impart proper biological activity and function. With regard to protein folding and post-translational processing, insect cells are second only to mammalian cell lines when expressing a eukaryotic protein, for example. The frequent use of baculovirus arises from the relative ease and speed with which a heterologous protein can be expressed on the laboratory scale and the high chance of obtaining a biologically active protein. Insect cells can be grown on serum free media which is an advantage in terms of costs as well as of biosafety. For large scale culture, conditions have been developed which meet the special requirements of insect cells.

In nature, baculoviruses are double-stranded DNA-containing viruses that infect a variety of different insect species. The nuclear polyhedrosis viruses, which comprise subgroup A of the Family Baculoviridae, induce the formation of paracrystalline occlusion bodies in the nuclei of infected host cells. These occlusion bodies are composed primarily of a single viral protein which is expressed at very high levels (polyhedrin). In later stages of the infection cycle, polyhedrin may account for more than 50% of the total protein in an infected cell. The polyhedrin gene has been cloned and sequenced and its unique features have provided the basis for the development of a series of baculovirus expression vectors (BEVs: Summers, M. D. and Smith, G. E., TAES Bull. 1555 (1987); Luckow, V. A. and Summers, M. D., Biotechnology 6:47-55 (1988); Miller, L. K., Ann. Rev. Microbiol. 42:177-179 (1988); U.S. Pat. No. 4,745,051, G. E. Smith and M. D. Summers (Filed May 27, 1983; Issued May 17, 1988)).

BEVs are recombinant baculoviruses in which the coding sequence for polyhedrin has been replaced with the coding sequence for a desired protein. In general, this approach involves the construction and isolation of recombinant baculoviruses in which the coding sequence for the chosen gene has been inserted behind the promoter for the nonessential polyhedrin viral gene (Pennica, et al, Mol. Cell. Biol. 4:399-406 (1984); Smith, et al, L. Virol. 46:584-593 (1983); Smith, G. E. and M. D. Summers, Mol. Cell. Biol. 3:2156-2165 (1983). Several advantages may exist when employing the BEV system. One of these advantages is the strong polyhedrin promoter which directs a high level of expression of the inserted heterologous nucleic acid encoding the target polypeptide. The newly expressed heterologous target protein accumulates in large amounts within these infected insect cells. Thus, as a result of the relative strength of the polyhedrin promoter, many different gene inserts can be expressed at very high levels.

In addition to providing a high expression level, another advantage of the BEV system is the ease with which these baculoviruses are produced and identified. This process begins by co-transfecting wild-type viral DNA and a "transfer vector" into susceptible host cells. A transfer vector is defined as a bacterial plasmid which contains a desired gene directly 3' to the polyhedrin promoter, as well as long viral sequences flanking the promoter on the 5' side. During cotransfection, homologous recombination occuring between viral and transfer vector DNA will produce a small percentage of viral genomes in which the polyhedrin gene has been replaced by the desired heterologous nucleic acid encoding the target polypeptide (0.1-5.0%). The wild-type progeny can be differentiated from the recombinant progeny by a conventional viral plaque assay. Recombinants in which the polyhedrin gene has been replaced, can be identified by their occlusion-negative plaque phenotype observed in a background of occlusion-positive wild-type plaques.

Because the polyhedrin gene is a non-essential gene for productive viral infection, another advantage of baculovirus expression vectors is that the recombinants are viable, helper-independent viruses. Also, baculoviruses only infect Lepidopteran insects; thus, they are noninfectious for vertebrates, and are, therefore, relatively safe genetic manipulation agents.

Notwithstanding the successes of BEVS and other systems for expression of heterologous proteins in insect and mammalian cell culture, maintenance of the viability of transformed or transfected cell cultures remains a capricious undertaking. Many laboratories refer to tissue culture as a "black art," due to the numerous variables that make it difficult to determine solutions when problems arise. An intensive and time-consuming systematic approach that examines the symptoms and meticulously retraces each step in the culture process is usually required to identify the material or critical procedure that has created the viability issue. Problems such as poor cell growth and abnormal morphology can result from materials that are poor quality, inappropriate, compromised, or contaminated and/or equipment that must be re-calibrated or re-setup to comply with manufacturer usage. Perhaps most frustrating, cells of different lots may react differently to standardized media and serum supplements resulting in unexpected toxicity or nutritional deficiency. Therefore, much of the time and expense invested in preparation of protein expression vectors may be lost when a protein production facility experiences difficulty in optimizing cell culture protein production conditions. As such it would be of great economic benefit to provide a generalized agent to a cell line to increase its viability, longevity and protein production capacity.

Insects, like other animals, have effective immune systems to combat both biotic and abiotic foreign invasion. Interestingly, endoparasitic insects spend a part of their life cycle inside the body of other insect hosts. Considerable effort has been expended investigating the mechanism by which these endoparasitic insects avoid the host immune system in this parasitic relationship.

One well characterized parasitoid-host system in which there is immune system evasion is that of the endoparasitic wasp *Campoletis sonorensis* and its host, the tobacco budworm *Heliothis virescens*. In investigating how immunosuppression is regulated in this system, it became apparent that a group of wasp viruses, known generically as polydnaviruses (PDVs), play a role in the suppression of the host immune system. Bracoviruses (BVs) and ichnoviruses (IVs) are the two main parasitic wasp associated PDVs. It is known that during oviposition, the endoparasitic insect, for example *C. sonorensis*, injects not only eggs but also polydnavirus and oviduct proteins. Shortly thereafter, the host insect immune system begins to show evidence of altered activity and the endoparasitoid eggs remain free from encapsulation. The precise mechanism of this immune suppression is not presently understood.

The WHv1.0, WHv1.6 and VHv1.1 genes of *C. sonorensis* polydnavirus (CsPDV) have been cloned and sequenced. These genes are described as members of a polydnavirus "cysteine-rich" gene family. (Dib-Hajj et al., Proc. Natl. Acad. Sci. (USA) 90: 3765 (1993)). It has been conjectured that these genes may play a role in preventing the recognition of foreign objects and/or the normal response of components of the immune system. (Summers et al., Proc. Natl. Acad. Sci. (USA) 92: 29 (1995)). Indeed, the VHv 1.1 gene product of the *C. sonorensis* polydnavirus has been implicated in the inhibition of the cellular immune response. This 30 kDa protein is shown by indirect immunofluorescence to bind both granulocytes and plasmatocytes and is thought to inhibit encapsulation. (Li et al., J. Virol., 68: 7482 (1994)).

Recent PDV genome sequencing projects have revealed a novel family of closely related genes that exist in several genomes including, but not limited to, the *C. sonorensis* IV (CsIV) *Hyposoter fugitivus* IV (HfIV), *Glypta fumiferana* IV (GfIV), *Microplitis demolitor* BV (MdBV), *Cotesia congregata* BV (CcBV), *Glyptapanteles indiensis* BV (GiBV), and *Toxoneuron nigriceps* BV (TnBV) genomes. This family of genes has been named vankyrins as their open reading frames (ORFs) encode proteins almost exclusively made up of ankyrin repeat domains. The PDV ankyrin repeat-carrying proteins show significant identity to the ankyrin repeats of the Iκβ family of transcription factor inhibitors suggesting that they disrupt intracellular NF-κβ mediated signal transduction cascades known to play a role in both vertebrate and invertebrate immune responses. There are seven vankyrin ORFs encoded by the CsIV genome.

The inventors have discovered that the expression of two CsIV vankyrins from a heterologous expression vector system increases the vitality, longevity, and therefore the protein productive capacity of cells in culture.

All references cited herein are hereby incorporated by reference in their entirety for all purposes.

SUMMARY OF THE INVENTION

One aspect of the invention relates to a vankyrin expression vector comprising a nucleic acid encoding the polypeptide of SEQ ID NO: 2. Another aspect of the invention relates to a vankyrin expression vector comprising a nucleic acid encoding the polypeptide of SEQ ID NO: 4. Yet another aspect of the invention relates to a vankyrin expression vector comprising a nucleic acid that hybridizes to the nucleic acid of SEQ ID NO: 1 under stringent conditions wherein the nucleic acid encodes a polypeptide capable of enhancing longevity and/or protein production of a cell line in which it is expressed. A further aspect of the invention relates to a vankyrin expression vector comprising a nucleic acid that hybridizes to the nucleic acid of SEQ ID NO: 3 under stringent conditions wherein the nucleic acid encodes a polypeptide capable of enhancing longevity and/or protein production of a cell line in which it is expressed. Another aspect of the invention relates to a vankyrin expression vector comprising a nucleic acid of SEQ ID NO: 1. Yet another aspect relates to a vankyrin expression vector comprising a nucleic acid of SEQ ID NO: 3.

Another aspect of the invention relates to a recombinant cell comprising a first nucleic acid selected from the group consisting of a nucleic acid encoding the polypeptide of SEQ ID NO: 2 a nucleic acid that hybridizes to the nucleic acid of SEQ ID NO: 1 under stringent conditions wherein the nucleic acid encodes a polypeptide capable of enhancing longevity and/or protein production of a cell line in which it is expressed; and a nucleic acid of SEQ ID NO: 1; and/or a second nucleic acid selected from the group consisting of: a nucleic acid encoding the polypeptide of SEQ ID NO: 4; a nucleic acid that hybridizes to the nucleic acid of SEQ ID NO: 3 under stringent conditions wherein the nucleic acid encodes a polypeptide capable of enhancing longevity and/or protein production of a cell line in which it is expressed; and a nucleic acid of SEQ ID NO: 3.

Another aspect of the invention relates to a method of enhancing target protein production of a cell line producing a target protein comprising transforming cells of the cell line with a vankyrin expression vector, growing the cell line; and isolating the target protein from the cell line.

Another aspect of the invention relates to a method of generating a recombinant cell line capable of enhanced target protein production comprising transforming a cell line with a heterologous nucleic acid encoding and driving the expression of a target protein; and transforming cells of the cell line with a vankyrin expression.

Yet another aspect of the invention relates to a method of generating a recombinant target protein-producing cell line capable of enhanced target protein production comprising constructing a vankyrin expression vector and transforming cells of the cell line with the vankyrin expression vector.

Another aspect of the invention relates to a method of enhancing longevity of a cell line producing a target protein comprising transforming cells of the cell line with a vankyrin expression vector, to obtain a transformed cell line producing a target protein; growing the transformed cell line producing a target protein longer than a the cell line not transformed with the vector.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail, in order not to unnecessarily obscure the present invention. Accordingly, the drawings and description are to be regarded as illustrative in nature, and not as restrictive.

BRIEF DESCRIPTION OF THE DRAWINGS

FIG. 2. Protein expression is extended in Sf9 cells infected with recombinant AcMNPV expressing Fat-Body specific CsIV ankyrin genes P-ank-1 and I²-ank-3. Western blots represent detection of proteins in freshly overlayed culture media presented to cells at each subsequent day following infection. The CsIV vankyrin genes are intracellular proteins and lack secretory signals, thus protein detected in the media overlay is the result of that released by cell lysis or rupture following infection. Delayed detection of proteins from P-ank-1 and I²-ank-3 viruses until day 3 p.i. is resultant of the enhanced longevity of Sf9 cells occurring early during infection by these viruses (as evidenced in FIG. 1).

FIG. 3. The cDNA and amino acid sequences of P-ank-1 (SEQ ID NO: 1 and 3, respectively) and I²-ank-3 (SEQ ID NO: 2 and 4, respectively).

FIG. 6. Shows the yield of recombinant vankyrin protein produced in cells infected by different recombinant AcMN-PVs. A cell line was infected with different recombinant AcMNPVs encoding different vankyrin proteins. Next, the vankyrin protein encoded by the each differing recombinant AcMNPV was isolated and quantified. The inventors note that cells infected by recombinant AcMNPVs encoding P-ank-1 and I²-ank-3 produced significantly larger quantities of their encoded CsIV vankyrin proteins, i.e., P-ank-1 and I²-ank-3 protein, respectively, than cells transgenically expressing the other CsIV vankyrin proteins.

DETAILED DESCRIPTION OF THE INVENTION

Figure 1:
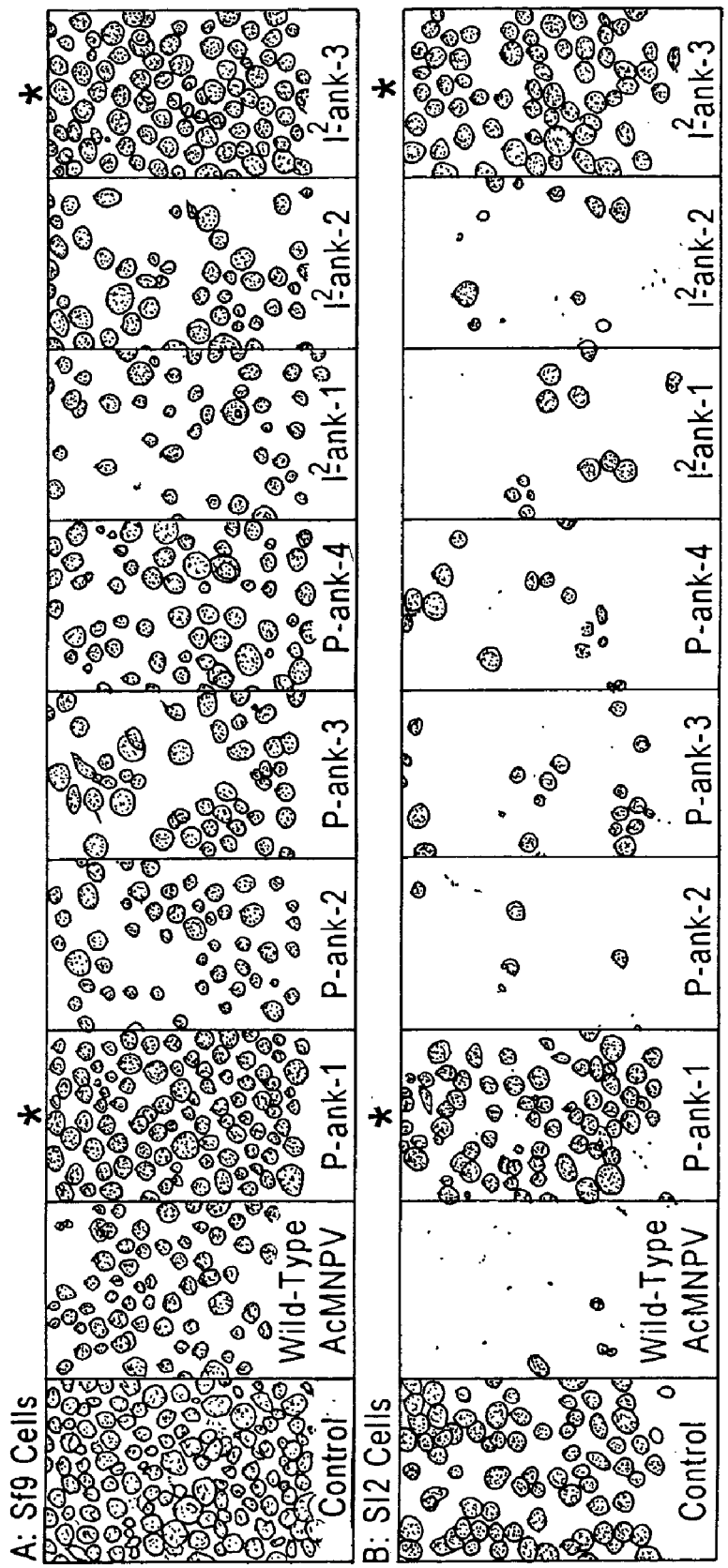
FIG. 1. Morphology of 4-day post infected (4 d p.i.) Sf9 (panel A) and S1-2 (panel B) cells exposed to recombinant AcMNPV's expressing CsIV vankyrin proteins. Cells infected with recombinant viruses expressing fat body specific P-ank-1 and I²-ank-3 proteins (asterisks) are more stable and resemble non-infected cells at 4 d p.i. Cells exposed to recombinant viruses expressing the remaining CsIV genes undergo apoptosis and lysis by 4 d p.i. and resemble cells infected with wild type AcMNPV. 40× magnification.

It is an object of the current invention to provide methods and compositions relating to the expression of vankyrin proteins in cell lines to increase their viability, longevity and capacity for protein production. The vankyrin gene family comprises 7 genes on CsIV genome segments P and I². Each vankyrin gene encodes an open reading frame of about 500-bp possessing 4 ankyrin repeat protein motifs. The vankyrin protein motifs show significant identities to ankyrin motifs of Cactus, the *Drosophila* IκB protein. MdBV and CsIV vankyrin genes align with the 4 C-terminal ankyrin repeat domains of IκBs but lack N-terminal repeats that function to mask nuclear localization signals (NLS) and sequester uninduced NF-κB dimers in the cytoplasm.

The seven vankyrin genes are I²-ank-1, I²-ank-2, I²-ank-3, P-ank-1, P-ank-2, P-ank-3 and P-ank-4. The inventors have discovered that the expression of P-ank-1 and I²-ank-3 proteins in cell culture has increased the cells' viability, longevity and, therefore, capacity for endogenous and/or heterologous target protein production. Specifically, the present invention relates to the enhanced expression of endogenous and/or heterologous target proteins/polypeptides in recombinant cells that are also expressing P-ank-1 and/or I²-ank-3 protein compared to expression host cells that are not expressing P-ank-1 and/or I²-ank-3 protein.

Before describing the invention in greater detail the following definitions are set forth to illustrate and define the meaning and scope of the terms used to describe the invention herein:

The term "nucleic acid molecule" is meant to include DNA, RNA and mixed DNA-RNA sequences. In addition to the typically found A, T, U, G and C residues, a nucleic acid molecule may also include related residues such as, for example, inosine (I).

The term "polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide.

The term "promoter region" refers to a DNA sequence that functions to control the transcription of one or more nucleic acid sequences, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, calcium or cAMP responsive sites, and any other nucleotide sequences known to act directly or indirectly to regulate transcription from the promoter.

The term "heterologous DNA" or "heterologous RNA" refers to DNA or RNA that does not occur naturally as part of the genome or DNA or RNA sequence in which it is present, or in which it is found, a cell or location or locations in the genome or DNA or RNA sequence that differs from that which it is in found in nature. Heterologous DNA or RNA is not endogenous to the cell into which it is introduced, but has been obtained from another cell or synthetically or recombinantly produced. Generally, though not necessarily, such DNA encodes RNA and protein not normally produced by the cell in which the DNA is transcribed or expressed. Similarly exogenous RNA encodes protein not normally expressed in the cell in which the exogenous RNA is present. Heterologous DNA or RNA may also be referred to as foreign DNA or RNA. Any DNA or RNA that one of skill in the art would recognize as heterologous or foreign to the cell in which it is expressed is herein encompassed by the term heterologous DNA or heterologous RNA. Examples of heterologous DNA include, but are not limited to, DNA that encodes a protein, polypeptide, reporter nucleic acid sequence, transcriptional or translational regulatory sequences, selectable or traceable marker protein, such as a protein that confers drug resistance, RNA including mRNA and antisense RNA, and ribozymes.

The term "recombinant polynucleotide" as used herein refers to a polynucleotide of genomic, cDNA, semisynthetic or synthetic origin which, by virtue of its origin or manipulation: (1) is not associated with all or a portion of the polynucleotide with which it is associated in nature and/or (2) is linked to a polynucleotide other than that to which it is linked in nature. The term "cDNA" or "complementary DNA" refers to single stranded or double stranded DNA sequences obtained by reverse transcription of messenger RNA isolated from a donor cell. For example, treatment of messenger RNA with a reverse transcriptase such as AMV reverse transcriptase or M-MuLV reverse transcriptase in the presence of an oligonucleotide primer will furnish an RNA-DNA duplex which can be treated with RNase H, DNA polymerase and DNA ligase to generate double stranded cDNA. If desired, the double stranded cDNA can be denatured by conventional techniques such as shearing to generate single stranded cDNA.

The term "operably linked" refers to the linkage of a DNA segment to another DNA segment in such a way as to allow the segments to function in their intended manners. A DNA sequence encoding a gene product is operably linked to a regulatory sequence when it is ligated to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site, and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers may be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "target" protein or polypeptide, refers to a protein of interest that is expressed in the recombinant cells also expressing P-ank-1 and/or $I^2$-ank-3 protein. Preferably, the recombinant cell is used as bioreactor for the production of the target protein. The target protein may be an endogenous protein naturally produced by the host cell type. For example, if the host cell type is a hybridoma, the target protein may be a monoclonal antibody. Alternatively, the target protein can be encoded by a heterologous recombinant nucleic acid, e.g. a cDNA. In this case, the target protein will be a heterologous protein, i.e., one that is not naturally expressed by the host cell line.

Central to the invention is the "vankyrin expression vector." A vankyrin expression vector is any genetic element, e.g., a plasmid, chromosome, virus, capable of bringing about the expression of a P-ank-1 (SEQ ID NO: 2) and/or $I^2$-ank-3 (SEQ NO: 4) proteins or proteins substantially similar thereto, i.e., those having similar amino acid sequences and the same functionalities with regard to the ability to provide enhanced cell longevity and/or protein productive capacity. Preferably, proteins P-ank-1 (SEQ ID NO: 2) and $I^2$-ank-3 (SEQ NO: 4) are encoded by SEQ ID NO: 1 and SEQ NO: 3, respectively. The skilled artisan will also appreciate that invention also encompasses vankyrin expression vector sequences comprising sequences substantially identical to SEQ ID NOs: 1 and 3. Such sequences may differ from SEQ ID NOs: 1 and 3, respectively, with regard to the identity of at least one nucleotide base.

However, all polynucleotides sequences "substantially identical" to SEQ ID NOs: 1 and 3 hybridize under stringent conditions (as defined herein) to all or a portion of the complements of SEQ ID NOs: 1 and 3 (i.e., target sequences), respectively. The terms "hybridize(s) specifically" or "specifically hybridize(s)" refer to complementary hybridization between an oligonucleotide (e.g., a primer or labeled probe) and a target sequence. The term specifically embraces minor mismatches that can be accommodated by reducing the stringency of the hybridization media to achieve the desired priming for the PCR polymerases or detection of hybridization signal.

Under stringent hybridization conditions, only highly complementary, i.e., substantially identical nucleic acid sequences, hybridize. Preferably, such conditions prevent hybridization of nucleic acids having 3 or more mismatches out of 20 contiguous nucleotides, more preferably 2 or more mismatches out of 20 contiguous nucleotides, most preferably one or more mismatch out of 20 contiguous nucleotides. The hybridizing portion of the hybridizing nucleic acid is at least about 90%, preferably at least about 95%, or most preferably about at least about 98%, identical to the sequence of a target sequence, or its complement.

Hybridization of a nucleic acid to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

Moreover, vankyrin expression vector containing polynucleotides "substantially similar or identical" to SEQ ID NO: 1 and 3, respectively, are capable of providing a cell line with enhanced longevity and/or protein production capability. In one embodiment, when expressed in Sf9 or S1-2 cells, polynucleotides "substantially similar or identical" to SEQ ID NO: 1 and 3, respectively, are capable of improving the longevity of those cells to such an extent that they resemble non-transfected Sf9 or S1-2 cells, whereas Sf9 or S1-2 cells transfected with a vector not containing polynucleotides "substantially similar or identical" to SEQ ID NO: 1 and 3, respectively. Preferably, the vector is a baculovirus vector. In another embodiment, polynucleotides "substantially similar or identical" to SEQ ID NO: 1 and 3, respectively, are capable of providing enhanced protein production in a cell line in which they are expressed, relative to a host cell line transfected in a similar manner by a vector lacking such polynucleotides. For example, polynucleotides "substantially similar or identical" to SEQ ID NO: 1 and 3, respectively, when expressed in Sf9 or S1-2 cells, are capable providing enhanced protein production in those cells, relative to Sf9 or S1-2 cells transfected with a vector not containing polynucleotides "substantially similar or identical" to SEQ ID NO: 1 and 3, respectively.

The vankyrin expression vector contains sequences to facilitate expression of P-ank-1 and/or $I^2$-ank-3 proteins in the host cell. Such sequences differ depending on the host organism; they include promoter sequences, for example but not limited to a polyhedrin promoter, SV40 promoter, or a conditionally activated promoter such as a metallothionein promoter to effect transcription; enhancer sequences to increase transcription; ribosomal binding site sequences; and transcription and translation termination sequences. The vector may also optionally behave either as an autonomous unit of polynucleotide replication within a cell (i.e., capable of replication under its own control) or being rendered capable of replication by insertion into a host cell chromosome, having attached to it another polynucleotide segment, so as to bring about the replication. Suitable vectors include, but are not limited to, viruses, plasmids, bacteriophages, yeast artificial chromosomes (YACs), cosmids, and the like. Vectors may contain polynucleotide sequences which are necessary to effect ligation or insertion of the vector into a desired host cell and the expression of its coding region(s). Additionally, the vankyrin expression vector itself may also contain heterologous nucleic acids encoding and driving the expression of target heterologous proteins and/or reporter proteins.

The skilled artisan will recognize that a wide range of vectors may be constructed to permanently, constitutively, conditionally or transiently drive P-ank-1 and/or $I^2$-ank-3 expression in a wide range of insect and mammalian cell lines. The skilled artisan would know how to operably link the aforementioned sequences. It is to be understood that this invention is intended to include other forms of expression vectors, host cells and transformation techniques which serve equivalent functions and which become known to the art hereto.

The preferred "vankyrin expression vector" is part of a baculovirus expression system engineered to express P-ank-1 and/or $I^2$-ank-3 proteins und the control of a polyhedrin promoter in the cells it infects. Most, preferably, the baculovirus is an *Autographa californica* baculovirus (AcNPV), and expression of P-ank-1 and/or $I^2$-ank-3 protein is driven by a polyhedrin promoter. The baculovirus *Autographa californica* mono nuclear polyhedrosis virus (AcMNPV), used in the examples as the original source of viral DNA was isolated according to procedures described in G. E. Smith and M. D. Summers, Virology, 89:517-527 (1978) and G. E. Smith and M. D. Summers, J. Virol., 39:125-137 (1981). According to the preferred embodiment of this invention, a particular strain of AcMNPV, E2, is utilized. However, those skilled in the art who have the benefit of this disclosure will recognize that other baculoviruses and other baculovirus strains may also be suitably utilized to obtain viral DNA. In particular, it is expected that at least the closely related and naturally occurring strains, *Trichoplusia ni* MNPV, *Rachiplusia ou* MNPV, *Galleria mellonella* MNPV and any plaque-purified strains such as the M3' R9, S1 and S3 strains of AcMNPV isolated and characterized in G. E. Smith and M. D. Summers, J. Virol., 33:311-319 (1980), as well as *Bombyx mori* NPV (BmNPV) may be utilized to advantage. Further description of those and other strains are found in G. E. Smith and M. D. Summers, Virol., 89:517-527 (1978).

Plasmids for the aforementioned BEVS carrying SEQ ID NO: 1 and/or 3, or sequences substantially similar thereto, may be designed according to conventional techniques known in the art and as described in M. D. Summers and G. E. Smith, A Manual of Methods for Baculovirus Vectors and Insect Cell Culture Procedures, Texas Agricultural Experiment Station Bulletin No. 1555, Texas A&M University (1987) ("Bulletin No. 1555"). (See also V. A. Luckow and M. D. Summers, Virol., 170:31-39 (1989)). In the preferred embodiment, the Baculovirus Expression Vector System from BD Biosciences Pharmingen is used which employs a modified *Autographa californica* nuclear polyhedrosis virus (AcNPV) genome—BD BaculoGold™ DNA, and an appropriate transfer vector. The diversity of AcNPV-based transfer vectors, combined with available *S. frugiperda* Sf9 and Sf21 cell lines, establish baculovirus expression as a preferred system for functional eukaryotic gene expression and the large-scale production of recombinant proteins.

Although the methodology described herein is believed to contain sufficient detail to enable one skilled in the art to practice the present invention, the plasmids can be constructed and purified using standard recombinant DNA techniques described in T. Maniatis, E. F. Fritsch and J. Sambrook, Molecular Cloning: A Laboratory Manual, Cold Spring Harbor Laboratory (1982) under the current regulations described in United States Dept. of HEW, National Institute of Health (NIH) Guidelines for Recombinant DNA Research. These references include procedures for the following standard methods: cloning procedures with *E. coli* plasmids, transformation of *E. coli* cells, plasmid DNA purification, phenol extraction of DNA, ethanol precipitation of DNA, agarose gel electrophoresis, purification of DNA fragments from agarose gels, and restriction endonuclease and other DNA-modifying enzyme reactions. Accordingly, these available references are incorporated herein by reference.

A "reporter nucleic acid sequence" is a DNA molecule that expresses a detectable gene product, which may be reporter RNA or reporter protein. The detection may be accomplished by any method known to one of skill in the art. For example, detection of mRNA expression may be accomplished by using Northern blot analysis and detection of protein may be accomplished by staining with antibodies specific to the protein, e.g. Western blot analysis. Preferred reporter nucleic acid sequences are those that are readily detectable. A reporter nucleic acid sequence may be operably linked in a DNA construct with a regulatory DNA sequence such that detection of the reporter nucleic acid sequence product provides a measure of the transcriptional activity of the regulatory sequence. Examples of reporter nucleic acid sequences include, but are not limited to, those coding for alkaline phosphatase, chloramphenicol acetyl transferase (CAT), luciferase, beta-galactosidase and alkaline phosphatase.

The terms "transformed" or "transfected" are used interchangeably and refer to the process by which exogenous DNA or RNA is transferred or introduced into an appropriate host cell. Additionally, nucleic acids encoding other heterologous proteins may be introduced into the host cell. Such transfected cells include stably transfected cells wherein the inserted DNA is rendered capable of replication in the host cell. Typically, stable transfection requires that the exogenous DNA be transferred along with a selectable marker nucleic acid sequence, such as for example, a nucleic acid sequence that confers antibiotic resistance, which enables the selection of the stable transfectants. This marker nucleic acid sequence may be ligated to the exogenous DNA or be provided independently by simultaneous cotransfection along with the exogenous DNA. Transfected cells also include transiently expressing cells that are capable of expressing the RNA or DNA for limited periods of time. The transfection procedure depends on the host cell being transfected. It can include packaging the polynucleotide in a virus as well as direct uptake of the polynucleotide. Transformation can result in incorporation of the inserted DNA into the genome of the host cell or the maintenance of the inserted DNA within the host cell in plasmid form. Methods of transformation/transfection are well known in the art and include, but are not limited to, direct injection, such as microinjection, viral infection, particularly replication-deficient adenovirus infection, electroporation, lipofection, calcium phosphate-mediated direct uptake and the like.

The term "host cell" generally refers to eukaryotic cells and includes any transformable cell which is capable of expressing a P-ank-1 and/or $I^2$-ank-3 proteins and can be, or has been, used as a recipient for a vankyrin expression vector. Once cells have transiently or stably taken up the vankyrin expression vector they are "recombinant" cells. DNA is commonly transferred or introduced into recipient mammal cells by calcium phosphate-mediated gene transfer, electroporation, lipofection, viral infection and the like. General methods, vectors and general considerations for gene transfer and expression may be found in M. Kriegler, Gene Transfer and Expression: A Laboratory Manual, Stockton Press (1990). Direct gene transfer to cells in vivo is achieved by the use of modified viral vectors, including retroviruses, adenoviruses, adeno-associated viruses and herpes viruses, liposomes, and direct injection of DNA into certain cell types. See, e.g., Wilson, Nature, 365: 691-692 (1993); Plautz et al, Annals NY Acad. Sci., 716: 144-153 (1994); Farhood et al, Annals NY Acad. Sci., 716: 23-34 (1994) and Hyde et al Nature, 362: 250-255 (1993).

Recombinant cells provided by this invention expressing P-ank-1 and/or $I^2$-ank-3 proteins are intended to produce target polypeptides, preferably human proteins and fragments thereof. The process involves culturing the recombinant cells under conditions wherein the endogenous or heterologous target proteins are expressed, e.g., by inducing the activity of a conditional promoter, and purifying the target protein from the cell culture. Purification of target proteins is within the skill set or the skilled artisan and generally involves the steps of cell lysis, homogenization, centrifugation and separation of the desired protein by processes such as salt fractionation, precipitation, and a variety of chromatographic methods such as anion exchange chromatography, hydrophobic interaction chromatography, high resolution chromatography, gel filtration chromatography and the like.

One aspect of this invention, relates to cells transiently expressing a vankyrin expression vector. In one embodiment of this aspect of the invention, the transient expression of the P-ank-1 and/or $I^2$-ank-3 proteins serves to temporarily strengthen the vitality of the culture expressing them. It is envisaged that this temporary increase in vitality will allow for the increased production of target proteins produced by and harvested from the host cell line. For example, an established monoclonal antibody (Mab)-producing hybridoma cell line may be transiently transfected with the vankyrin expression element to obtain an increase in antibody production. The most simple method for in vitro production of Mabs is standard tissue culture in either large flasks or roller bottles. The production of Mab by hybridomas in tissue culture is hybridoma-dependent and can vary between 1-100 μg/ml. Therefore, it is often necessity to concentrate Mab from supernatant. Transfecting a hybridoma with the vankyrin expression element will allow for increased Mab production and lessen the need for a technician to concentrate antibody in the supernatant.

In another embodiment of this aspect of the invention, the cells transiently transfected with a vankyrin expression vector are also transiently or permanently co-transfected with an additional expression element having a heterologous nucleic acid sequence encoding and driving the expression of a heterologous target protein.

Another aspect of the invention relates to cells in which a vankyrin expression element is stably integrated into the cells' genome, thus rendering a recombinant cell line that provides superior protein productive capacity when compared to its wild type cell counterpart. In one embodiment of this aspect of the invention, such a cell line is amenable to further permanent transfection with an additional expression vector carrying a nucleic acid sequence encoding a target protein of interest. In another embodiment, such a cell line is amenable to transient transfection with an additional expression vector carrying a nucleic acid sequence encoding a target protein of interest. In another embodiment, the target proteins produced by and harvested from the cells having permanently integrated vankyrin expression vectors may be proteins endogenously produced by the host cells themselves.

Yet a further aspect of the invention relates to a vankyrin expression vector that contains additional nucleic acid sequences encoding one or more heterologous target proteins of interest. Such a vector could be permanently or transiently introduced into a host cell line.

The recombinant cells having the "vankyrin expression vector" expressing P-ank-1 and/or $I^2$-ank-3 proteins are mammalian, such as, but not limited to Chinese hamster ovary (CHO) cells, COS-7 cells, fibroblasts as well as C127, 3T3, CHO, HeLa and BHK cell lines. Most preferably, the cells are insect cells such as, but not limited to S2 cells, Schneider cells, S12 cells, 5B1-4, Tn5, and Sf9 cells. The *Spodoptera frugiperda* Sf9 cell line may be obtained from American Type Culture Collection (Rockville, Md.) and is assigned accession number ATCC CRL 1711. See M. D. Summers and G. E. Smith, Bulletin No. 1555, suora. Those skilled in the art who have the benefit of this disclosure will recognize that other clonal derivatives of the Sf9 cell line as well as *Trichoplusia ni* and other insects such as the silkworm, *Bombyx mori*, or insect cell cultures derived there from can be used to advantage.

The standard methods of insect cell culture, cotransfection and preparation of plasmids in accordance with the examples, are set forth in M. D. Summers and G. E. Smith, A Manual of Methods for Baculovirus Vectors and Insect Cell Culture Procedures, Texas Agricultural Experiment Station Bulletin No. 1555, Texas A&M University (1987). This reference also pertains to the standard methods of cloning genes into AcM-NPV transfer vectors, plasmid DNA isolation, transferring genes into the AcMNPV genome, viral DNA purification, radiolabelling recombinant proteins and preparation of insect cell culture media. Accordingly, this available reference is incorporated herein by reference.

The procedures for the cultivation of viruses and cells are described in L. E. Volkman and M. D. Summers, J. Virol, 19:820-832 (1975) and L. E. Volkman, M. D. Summers and C. H. Hsieh, J. Virol, 19:820-832 (1976). Viral growth kinetics were determined as described by L. E. Volkman, et al., suora, using *S. frugiperda* and a 1.5% agarose overlay.

Example 1

Figure 4:
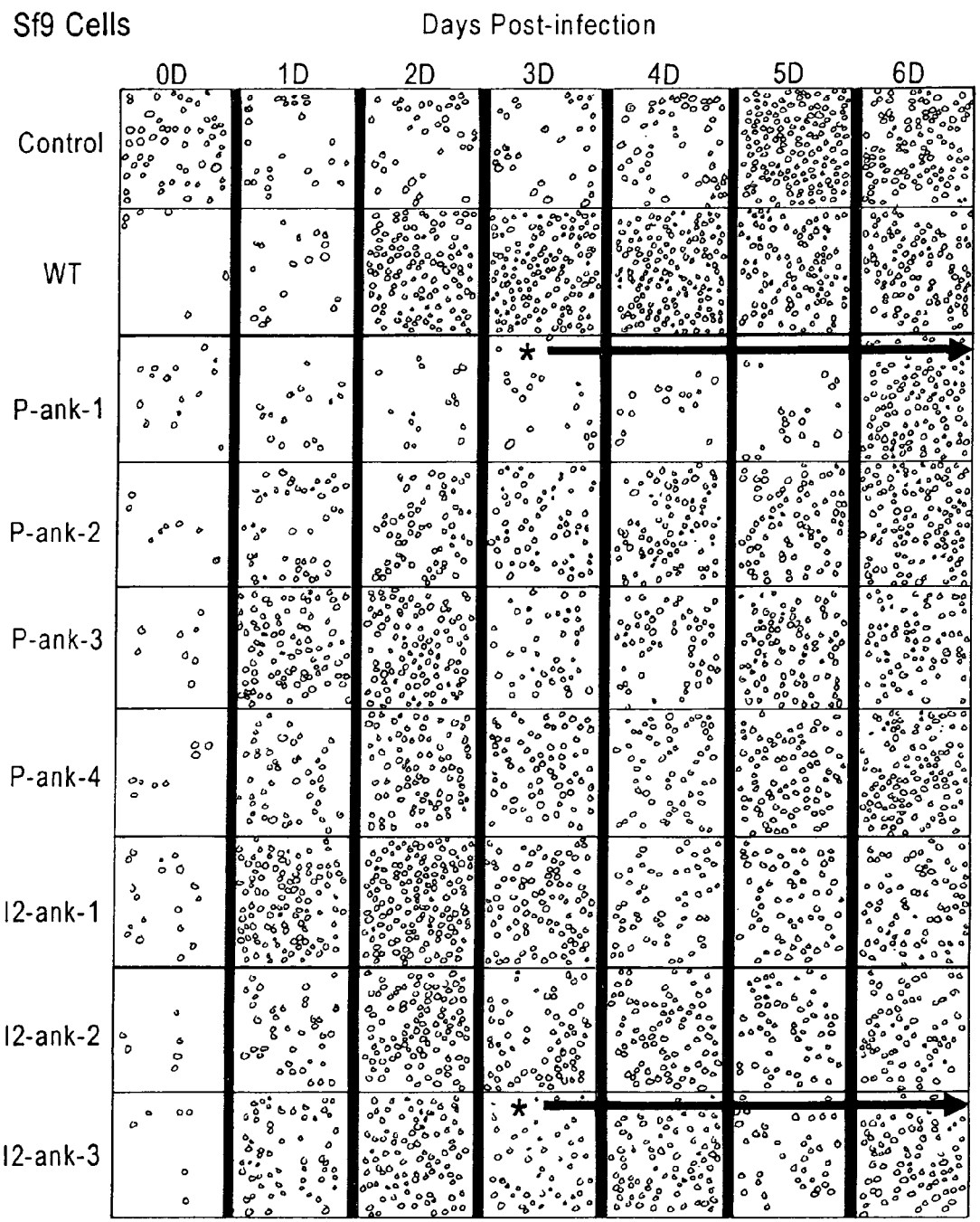
FIG. 4. Morphology of Sf9 cells exposed to recombinant AcMNPV's expressing CsIV vankyrin proteins over time. Cells infected with recombinant viruses expressing fat body specific P-ank-1 and I²-ank-3 proteins (asterisks) are more stable and increase the longevity of the cells through 6 days (6 D) post infection such that they resemble non-transfected control cells. Cells exposed to recombinant viruses expressing the remaining CsIV genes undergo apoptosis and lysis by 4 d p.i. and resemble cells infected with wild type AcMNPV. 40× magnification.
Figure 5:
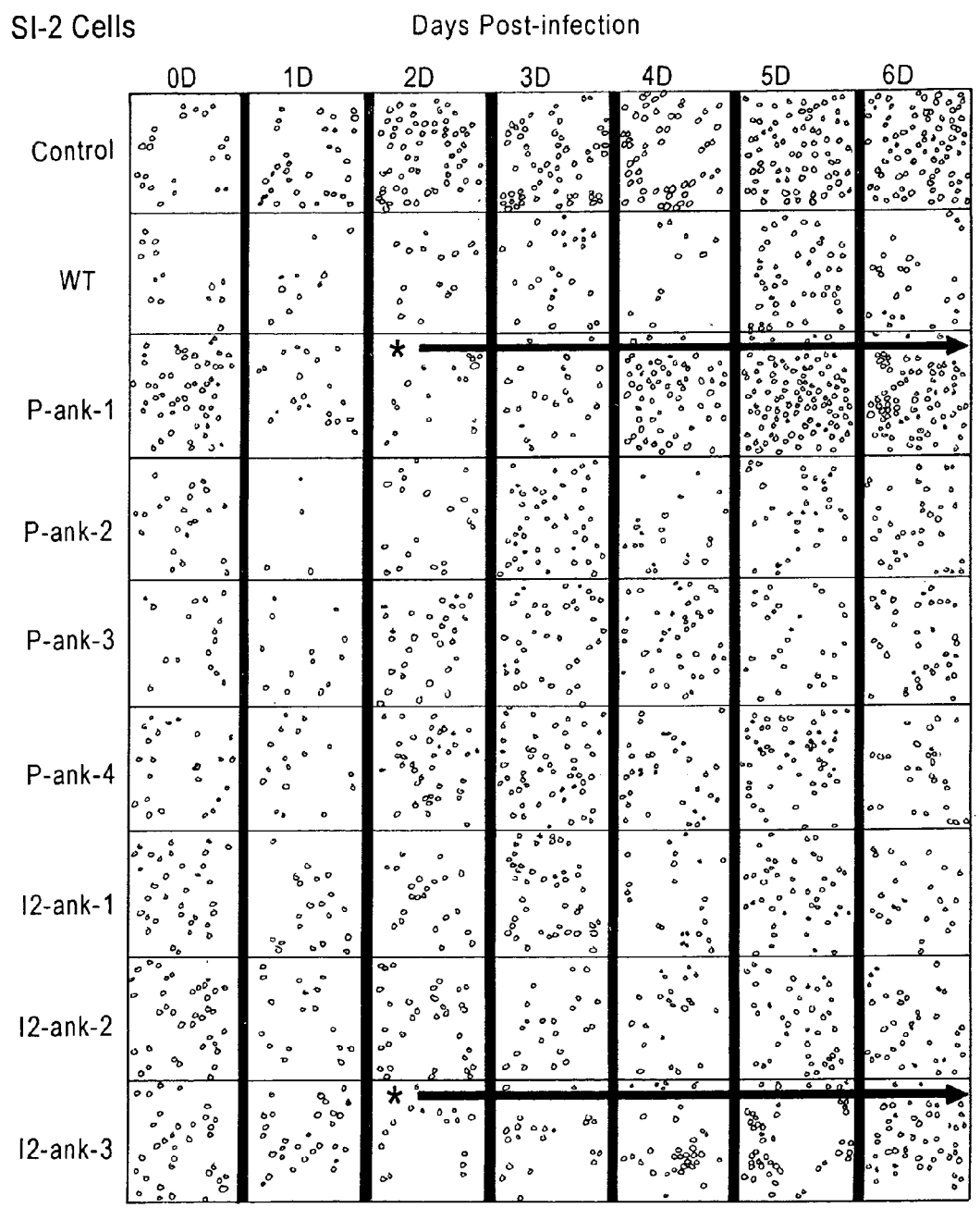
FIG. 5. Morphology of S1-2 cells exposed to recombinant AcMNPV's expressing CsIV vankyrin proteins over time. Cells infected with recombinant viruses expressing fat body specific P-ank-1 and I²-ank-3 proteins (asterisks) are more stable and maintain the vitality of the cells through 6 days (6 D) post infection such that they resemble non-transfected control cells. Cells exposed to recombinant viruses expressing the remaining CsIV genes undergo apoptosis and lysis by 4 d p.i. and resemble cells infected with wild type AcMNPV. 40× magnification.

For example, when expressed in Sf9 or S1-2 cells, polynucleotides "substantially similar or identical" to SEQ ID NO: 1 and 3, respectively, are capable improving the longevity of those cells to such an extent that they resemble non-transfected Sf9 or S1-2 cells, whereas Sf9 or S1-2 cells transfected with a vector not containing polynucleotides "substantially similar or identical" to SEQ ID NO: 1 and 3, respectively, rapidly lyse about 4 days post infection. FIG. 1. Moreover, the longevity of a cell line expressing polynucleotides "substantially similar or identical" to SEQ ID NO: 1 and 3, respectively, continues to be maintained such that it resembles non-infected cells at about 6 to about 7 days post infection. FIGS. 2, 4 and 5. Therefore, when an Sf9 or S1-2 cell line is infected with a AcMNPV comprising polynucleotides "substantially similar or identical" to SEQ ID NO: 1 or 3, respectively, the infected Sf9 or S1-2 cell line has enhanced longevity relative to an Sf9 or S1-2 cell line infected with a wild type AcMNPV.

Example 2

Polynucleotides "substantially similar or identical" to SEQ ID NO: 1 and 3, respectively, are capable of providing enhanced protein production in a cell line in which they are expressed, relative to a host cell line transfected in a similar manner by a vector lacking such polynucleotides. Specifically, polynucleotides "substantially similar or identical" to SEQ ID NO: 1 and 3, respectively, when expressed in Sf9 or S1-2 cells, are capable providing enhanced protein production in those cells, relative to Sf9 or S1-2 cells transfected with a vector not containing polynucleotides "substantially similar or identical" to SEQ ID NO: 1 and 3, respectively. As can be seen in FIG. 2, protein expression is extended in Sf9 cells infected with recombinant AcMNPV expressing CsIV ankyrin genes P-ank-1 and $I^2$-ank-3. Western blots in FIG. 2, represent detection of proteins in freshly overlayed culture media presented to cells at each subsequent day following infection. The CsIV vankyrin genes are intracellular proteins and lack secretory signals, thus protein detected in the media overlay is the result of that released by cell lysis or rupture following infection. Delayed detection of proteins from P-ank-1 and $I^2$-ank-3 viruses until day 3 post infection is resultant of the enhanced longevity of Sf9 cells occurring early during infection by these viruses (as evidenced in FIG. 1). Additionally, because cells expressing polynucleotides "substantially similar or identical" to SEQ ID NO: 1 and 3, respectively, are able to produce proteins for a longer period of time, they are able to produce more protein in total, thus providing an enhanced protein production capability. Therefore, when an Sf9 or S1-2 cell line is infected with a AcMNPV comprising polynucleotides "substantially similar or identical" to SEQ ID NO: 1 or 3, respectively, the infected Sf9 or S1-2 cell line has enhanced protein production relative to an Sf9 or S1-2 cell line infected with a wild type AcMNPV.

What is claimed is:

1. A vankyrin expression vector comprising the nucleic acid sequence encoding the polypeptide of SEQ ID NO: 2 and a nucleic acid encoding the polypeptide of SEQ ID NO: 4.

2. A vankyrin expression vector comprising the nucleic acid sequence encoding the polypeptide of SEQ ID NO: 4.

3. A vankyrin expression vector comprising a first nucleic acid that hybridizes to the full-length complement of the nucleic acid of SEQ ID NO: 1 under stringent conditions comprising hybridizing at 68° C. in 5×SSC/5×Denhardt's solution/1.0% SDS, and washing in 0.2×SSC/0.1% SDS at room temperature; and a second nucleic acid that hybridizes to the full-length complement of SEQ ID NO: 3 under stringent conditions comprising hybridizing at 680 in 5×SSC/5×Denhardt's solution/1.0% SDS, and washing in 0.2×SSC/0.1% SDS at room temperature; wherein the first and second nucleic acids each encode a polypeptide capable of enhancing longevity of a cell line in which it is expressed and/or enhancing production of one or more target proteins optionally encoded by the vector compared to wild type cell counterpart of the cell line.

4. A vankyrin expression vector comprising a nucleic acid that hybridizes to the full-length complement of SEQ ID NO: 3 under stringent conditions comprising hybridizing at 680 in 5×SSC/5×Denhardt's solution/1.0% SDS, and washing in 0.2×SSC/0.1% SDS at room temperature; wherein the nucleic acid encodes a polypeptide capable of enhancing longevity of a cell line in which it is expressed and/or enhancing production of one or more target proteins optionally encoded by the vector compared to wild type cell counterpart of the cell line.

5. A vankyrin expression vector comprising the nucleic acid sequence of SEQ ID NO: 1 and the nucleic acid sequence of SEQ ID NO: 3.

6. A vankyrin expression vector comprising the nucleic acid sequence of SEQ ID NO: 3.

7. The vankyrin expression vector of any one of claims 1 to 6 wherein the vankyrin expression vector is a baculovirus vankyrin expression vector.

8. The vector of any one of claims 1 to 6, wherein said vector further comprises a nucleic acid encoding a target protein.

9. A recombinant cell line comprising any one of the vectors of claims 1 to 6.

10. A method of enhancing target protein production of a cell line producing a target protein comprising:
   a. transforming cells of said cell line with a vankyrin expression vector comprising a first polynucleotide encoding one or more target proteins; said vankyrin expression vector further comprising a second polynucleotide selected from the group consisting of:
      i. a nucleic acid encoding the polypeptide of SEQ ID NO: 2 and the polypeptide of SEQ ID NO: 4;
      ii. a first nucleic acid sequence that hybridizes to the nucleic acid of SEQ ID NO: 1 under stringent conditions comprising hybridizing at 68° in 5×SSC/5×Denhardt's solution/1.0% SDS, and washing in 0.2×SSC/0.1% SDS at room temperature and a second nucleic acid sequence that hybridizes to SEQ ID NO: 3 under stringent conditions comprising hybridizing at 68° in 5×SSC/5×Denhardt's solution/1.0% SDS, and washing in 0.2×SSC/0.1% SDS at room temperature; wherein the first and second nucleic acid sequences each encode a polypeptide capable of enhancing longevity and/or protein production of a cell line in which it is expressed, compared to wild type cell counterpart of the cell line;
      iii. a nucleic acid comprising SEQ ID NO: 1 and SEQ ID NO:3;
      iv. a nucleic acid encoding the polypeptide of SEQ ID NO: 4;
      v. a nucleic acid that hybridizes to the nucleic acid of SEQ ID NO: 3 under stringent conditions comprising hybridizing at 680 in 5×SSC/5×Denhardt's solution/1.0% SDS, and washing in 0.2×SSC/0.1% SDS at room temperature; wherein the nucleic acid encodes a polypeptide capable of enhancing longevity and/or protein production of a cell line in which it is expressed, compared wild type cell counterpart of the cell line; and
      vi. the nucleic acid of SEQ ID NO: 3;
   b. growing said cell line; and
   c. isolating said target protein from said cell line.

11. A method of generating a recombinant cell line capable of enhanced target protein production comprising:
   a. transforming a cell line with a heterologous nucleic acid encoding and expressing one or more target proteins; and
   b. transforming cells of said cell line with a vankyrin expression vector; said vankyrin expression vector comprising a polynucleotide selected from the group consisting of:
      i. a nucleic acid encoding the polypeptide of SEQ ID NO: 2 and the polypeptide of SEQ ID NO: 4;
      ii. a first nucleic acid sequence that hybridizes to the nucleic acid of SEQ ID NO: 1 under stringent conditions comprising hybridizing at 68° in 5×SSC/5×Denhardt's solution/1.0% SDS, and washing in 0.2×SSC/0.1% SDS at room temperature and a second nucleic acid sequence that hybridizes to SEQ ID NO: 3 under stringent conditions comprising hybridizing at 680 in 5×SSC/5×Denhardt's solution/1.0% SDS, and washing in 0.2×SSC/0.1% SDS at room temperature; wherein the first and second nucleic acid sequences each encode a polypeptide capable of enhancing longevity and/or protein production of a cell line in which it is expressed, compared to wild type cell counterpart of the cell line;

iii. a nucleic acid comprising SEQ ID NO: 1 and SEQ ID NO: 3;
iv. a nucleic acid encoding the polypeptide of SEQ ID NO: 4;
v. a nucleic acid that hybridizes to the nucleic acid of SEQ ID NO: 3 under stringent conditions comprising hybridizing at 680 in 5×SSC/5×Denhardt's solution/1.0% SDS, and washing in 0.2×SSC/0.1% SDS at room temperature; wherein the nucleic acid encodes a polypeptide capable of enhancing longevity and/or protein production of a cell line in which it is expressed, compared to wild type cell counterpart of the cell line; and
vi. the nucleic acid of SEQ ID NO: 3.

12. A method of generating a recombinant target protein-producing cell line capable of enhanced target protein production comprising:
a. constructing a vankyrin expression vector; said vankyrin expression vector comprising a polynucleotide selected from the group consisting of:
i. a nucleic acid encoding the polypeptide of SEQ ID NO: 2 and the polypeptide of SEQ ID NO: 4;
ii. a first nucleic acid sequence that hybridizes to the nucleic acid of SEQ ID NO: 1 under stringent conditions comprising hybridizing at 680 in 5×SSC/5×Denhardt's solution/1.0% SDS, and washing in 0.2×SSC/0.1% SDS at room temperature and a second nucleic acid sequence that hybridizes to the nucleic acid of SEQ ID NO: 3 under stringent conditions comprising hybridizing at 68° in 5×SSC/5×Denhardt's solution/1.0% SDS, and washing in 0.2×SSC/0.1% SDS at room temperature; wherein the first and second nucleic acid sequences each encode a polypeptide capable of enhancing longevity and/or protein production of a cell line in which it is expressed, compared to wild type cell counterpart of the cell line;
iii. a nucleic acid comprising SEQ ID NO: 1 and SEQ ID NO: 3;
iv. a nucleic acid encoding the polypeptide of SEQ ID NO: 4;
v. a nucleic acid that hybridizes to the nucleic acid of SEQ ID NO: 3 under stringent conditions comprising hybridizing at 68° in 5×SSC/5×Denhardt's solution/1.0% SDS, and washing in 0.2×SSC/0.1% SDS at room temperature; wherein the nucleic acid encodes a polypeptide capable of enhancing longevity and/or protein production of a cell line in which it is expressed, compared to wild type cell counterpart of the cell line; and
vi. the nucleic acid of SEQ ID NO: 3; and
b. transforming cells of said cell line with the vankyrin expression vector.

13. A method of enhancing longevity of a cell line producing a target protein comprising:
a. transforming cells of said cell line with a vankyrin expression vector, said vankyrin expression vector comprising a polynucleotide selected from the group consisting of:
i. a nucleic acid encoding the polypeptide of SEQ ID NO: 2 and the polypeptide of SEQ ID NO: 4;
ii. a first nucleic acid sequence that hybridizes to the nucleic acid of SEQ ID NO: 1 under stringent conditions comprising hybridizing at 680 in 5×SSC/5×Denhardt's solution/1.0% SDS, and washing in 0.2×SSC/0.1% SDS at room temperature and a second nucleic acid sequence that that hybridizes to the nucleic acid of SEQ ID NO: 3 under stringent conditions comprising hybridizing at 680 in 5×SSC/5×Denhardt's solution/1.0% SDS, and washing in 0.2×SSC/0.1% SDS at room temperature; wherein the first and second nucleic acid sequences each encode a polypeptide capable of enhancing longevity and/or protein production of a cell line in which it is expressed, compared to wild type cell counterpart of the cell line;
iii. a nucleic acid sequence comprising SEQ ID NO: 1 and SEQ ID NO: 3;
iv. a nucleic acid encoding the polypeptide of SEQ ID NO: 4;
v. a nucleic acid that hybridizes to the nucleic acid of SEQ ID NO: 3 under stringent conditions comprising hybridizing at 68° in 5×SSC/5×Denhardt's solution/1.0% SDS, and washing in 0.2×SSC/0.1% SDS at room temperature; wherein the nucleic acid encodes a polypeptide capable of enhancing longevity and/or protein production of a cell line in which it is expressed, compared to wild type cell counterpart of the cell line; and
vi. the nucleic acid of SEQ ID NO: 3; and
b. obtaining a transformed cell line having a longevity greater than the same cell line lacking said vankyrin expression vector.

14. The method of any one of claims 10-13 wherein said cell line is an *Spodoptora frugiperda* 9 (Sf9) or an *Spodoptera littoralis* 2 cell line.

15. The method of any one of claims 10-13 wherein said vector is a baculovirus expression vector.

16. The method of any one of claims 10-13 wherein the vector is stably transfected or transformed.

17. The method of any one of claims 10-13, wherein the target protein is encoded by a polynucleotide that is heterologous to the cell line.

18. The method of any one of claims 10, 12 or 13 wherein said target protein is an endogenous protein to the cell line.

19. The method of any one of claims 10-13 wherein the vector is transiently transfected.

20. An isolated nucleic acid encoding the polypeptide is of SEQ ID NO: 2 and the polypeptide of SEQ ID NO:4.

21. An isolated nucleic acid encoding a polypeptide having the sequence of SEQ ID NO: 4.

22. An isolated nucleic acid comprising a first nucleotide sequence that hybridizes to the full length complement of SEQ ID NO: 1 under stringent conditions comprising hybridizing at 68° in 5×SSC/5×Denhardt's solution/1.0% SDS, and washing in 0.2×SSC/0.1% SDS at room temperature and a second nucleic acid sequence that hybridizes to the full length complement of SEQ ID NO: 3 under stringent conditions comprising hybridizing at 680 in 5×SSC/5×Denhardt's solution/1.0% SDS, and washing in 0.2×SSC/0.1% SDS at room temperature; wherein the first and second nucleic acid sequences each encodes a single polypeptide capable of enhancing longevity of a cell line in which it is expressed, compared to wild type cell counterpart of the cell line.

23. An isolated nucleic acid that hybridizes to the full length complement of SEQ ID NO: 3 under stringent conditions comprising hybridizing at 68° in 5×SSC/5×Denhardt's solution/1.0% SDS, and washing in 0.2×SSC/0.1% SDS at room temperature; wherein the nucleic acid encodes a polypeptide capable of enhancing longevity of a cell line in which it is expressed, compared to wild type cell counterpart of the cell line.

24. An isolated nucleic acid consisting of SEQ ID NO: 3.

* * * * *